(12) United States Patent
Shih et al.

(10) Patent No.: US 8,556,822 B2
(45) Date of Patent: Oct. 15, 2013

(54) REEL-TYPE BLOOD PRESSURE CUFF

(75) Inventors: Yi-Cheng Shih, Chiayi (TW); Feng-Chi Liu, Xindian (TW); Yi-Chin Tsai, Banqiao (TW)

(73) Assignee: Quanta Computer Inc., Taoyuan Shien (TW)

( * ) Notice: Subject to any disclaimer, the term of this patent is extended or adjusted under 35 U.S.C. 154(b) by 544 days.

(21) Appl. No.: 12/923,063

(22) Filed: Aug. 31, 2010

(65) Prior Publication Data

US 2011/0257541 A1 Oct. 20, 2011

(30) Foreign Application Priority Data

Apr. 15, 2010 (TW) ................ 99206838 U (51) Int. Cl.
*A61B 5/00* (2006.01)
*A61B 5/02* (2006.01)
*A61B 17/00* (2006.01)

(52) U.S. Cl.
USPC ........... 600/499; 600/301; 600/490; 600/491; 600/492; 600/495; 606/202

(58) Field of Classification Search
USPC ........... 600/301, 490–492, 499, 495; 606/202
See application file for complete search history.

(56) References Cited

U.S. PATENT DOCUMENTS

| | | | | |
|---|---|---|---|---|
| 4,206,765 A | * | 6/1980 | Huber | 600/490 |
| 6,575,913 B1 | * | 6/2003 | Woolley | 600/490 |
| 6,827,688 B2 | * | 12/2004 | Goto et al. | 600/485 |
| 2003/0078507 A1 | * | 4/2003 | Sadritabrizi | 600/499 |
| 2004/0260187 A1 | * | 12/2004 | Sano et al. | 600/499 |
| 2005/0131310 A1 | * | 6/2005 | Freund et al. | 600/499 |
| 2007/0038133 A1 | * | 2/2007 | Kishimoto et al. | 600/490 |
| 2009/0062668 A1 | * | 3/2009 | Todokoro et al. | 600/499 |
| 2011/0009757 A1 | * | 1/2011 | Sano et al. | 600/499 |

* cited by examiner

*Primary Examiner* — Patricia Mallari
*Assistant Examiner* — Puya Agahi
(74) *Attorney, Agent, or Firm* — Rabin & Berdo, P.C.

(57) ABSTRACT

A blood pressure measuring device disclosed in the present invention comprises a base, a reel-type cuff and at least one stopper. The reel-type cuff is elastically and recoverably reeled in the base with one end, and is freely extended out from the base with the other end. The stopper, after being operated, can limit at least one determined length that the reel-type cuff is extended out from the base.

14 Claims, 8 Drawing Sheets

REEL-TYPE BLOOD PRESSURE CUFF

RELATED APPLICATIONS

This application claims priority to Taiwan Application Serial Number 99206838, filed Apr. 15, 2010, which is herein incorporated by reference.

BACKGROUND

1. Technical Field

The present invention relates to a physiological information measuring device, more particularly to a blood pressure measuring device.

2. Description of Related Art

When a blood pressure measuring device is served to measure blood pressure, an artery pressing bag is firstly reeled of an arm surface, then the artery pressing bag is inflated for pressing arm artery so as to retard the artery blood flow, afterwards the artery pressing bag is gradually depressurized and the blood flow of artery is recovered, such that the blood pressure measuring device can determine the blood pressure value through detecting the pressing wave of arm artery.

Because the blood pressure measuring device generally is served for more than one person, and each user has different arm size; as a result, several attempts of reeling the artery pressing bag have to be done till finding the most suitable and most comfortable length for reeling the arm if anyone who want to measure blood pressure, the blood pressure measurement is then processed. However, after several attempts for reeling the artery pressing bag on the arm, the arm may not be placed at the correct location of the artery pressing bag, thus the precision of blood pressure measurement is greatly reduced.

So how to develop a blood pressure measuring device capable of solving the mentioned disadvantages to enable the user correctly using the blood pressure measuring device for increasing the measurement precision shall be seriously concerned.

SUMMARY

One primary object of the present invention is to provide a blood pressure measuring device for rapidly positioning a human arm at a proper position of an artery pressing bag through providing various lengths of the artery pressing bag reeling on the human arm for increasing the precision of blood pressure measurement.

Another object of the present invention is to provide a blood pressure measuring device for reducing testing time for reeling an artery pressing bag on a human arm through limiting various determined lengths of the artery pressing bag reeling on the human arm so as to serve users having various arm sizes, for increasing the convenience of using the blood pressure measuring device.

Another object of the present invention is to provide a blood pressure measuring device, for saving the storing space for an artery pressing bag, improving the storage of the artery pressing bag, and further for shortening the managing time for packing up the artery pressing bag.

The blood pressure measuring device provided by the present invention comprises a base, a reel-type cuff capable of being elastically reeled in/out, a second fastening part and at least one stopper. The base is provided with an accommodating space therein and a first fastening part thereon. The reel-type cuff is elastically and recoverably reeled in the accommodating space with a first end thereof, and is out of the accommodating space with a second end thereof opposite to the first end. The stopper(s) are respectively moveably installed on the base for limiting different determined lengths that the reel-type cuff is extended out from the accommodating space when the stoppers are respectively physically contacted with the reel-type cuff in the accommodating space.

DESCRIPTION OF THE PREFERRED EMBODIMENTS

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 1:
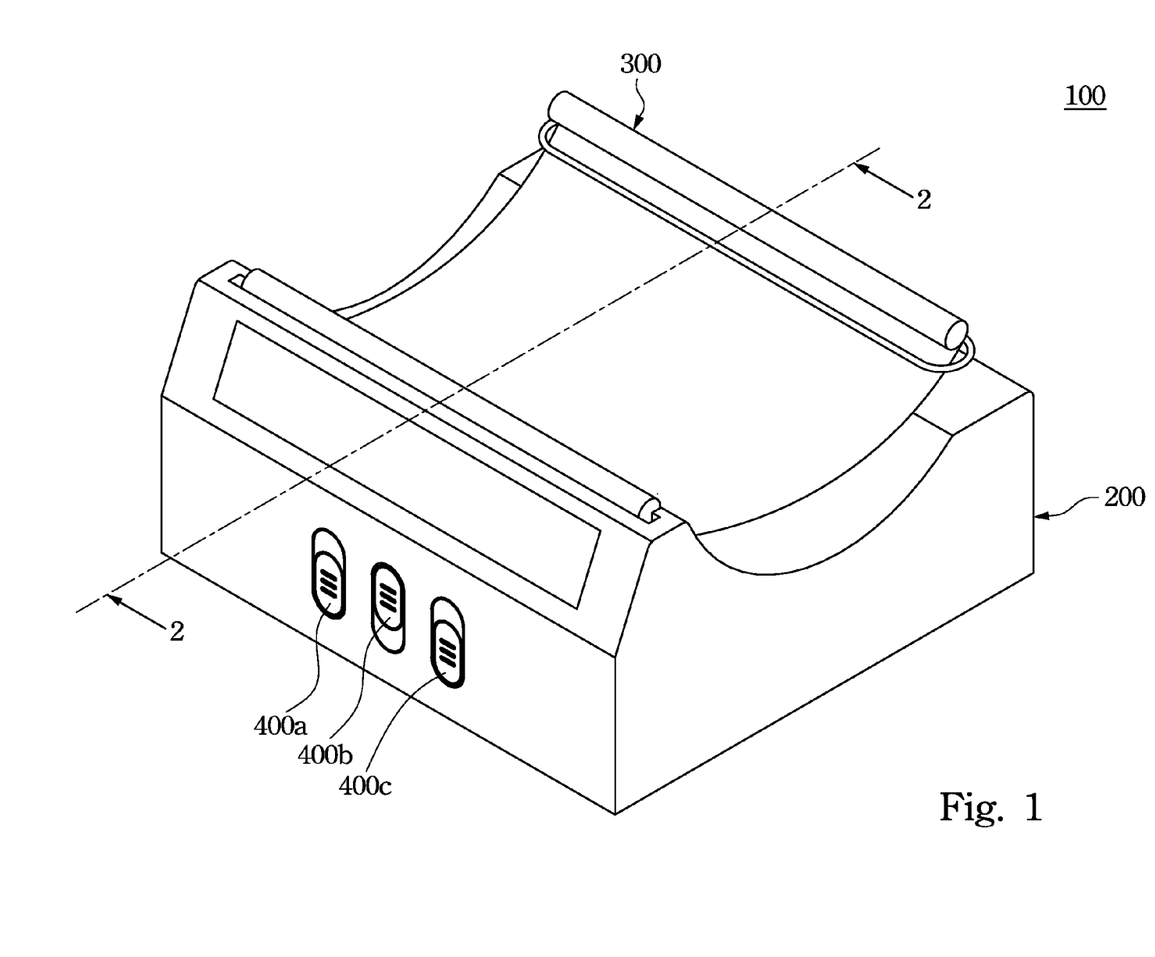
FIG. 1 is an appearance view of the blood pressure measuring device of one embodiment of the present invention, when not being operated.
Figure 2:
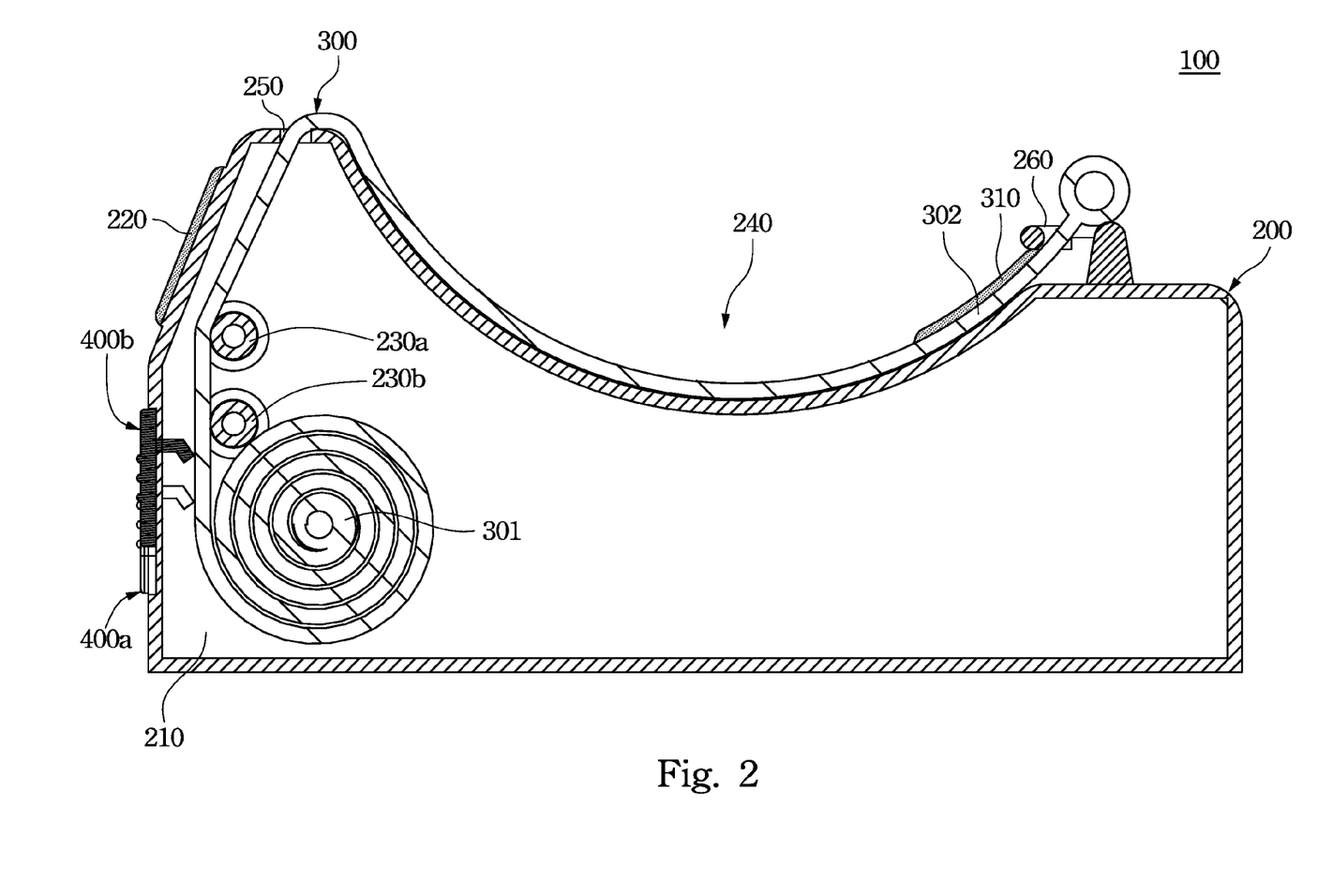
FIG. 2 is a cross sectional view of FIG. 1 along a 2-2 section line.
Figure 3:
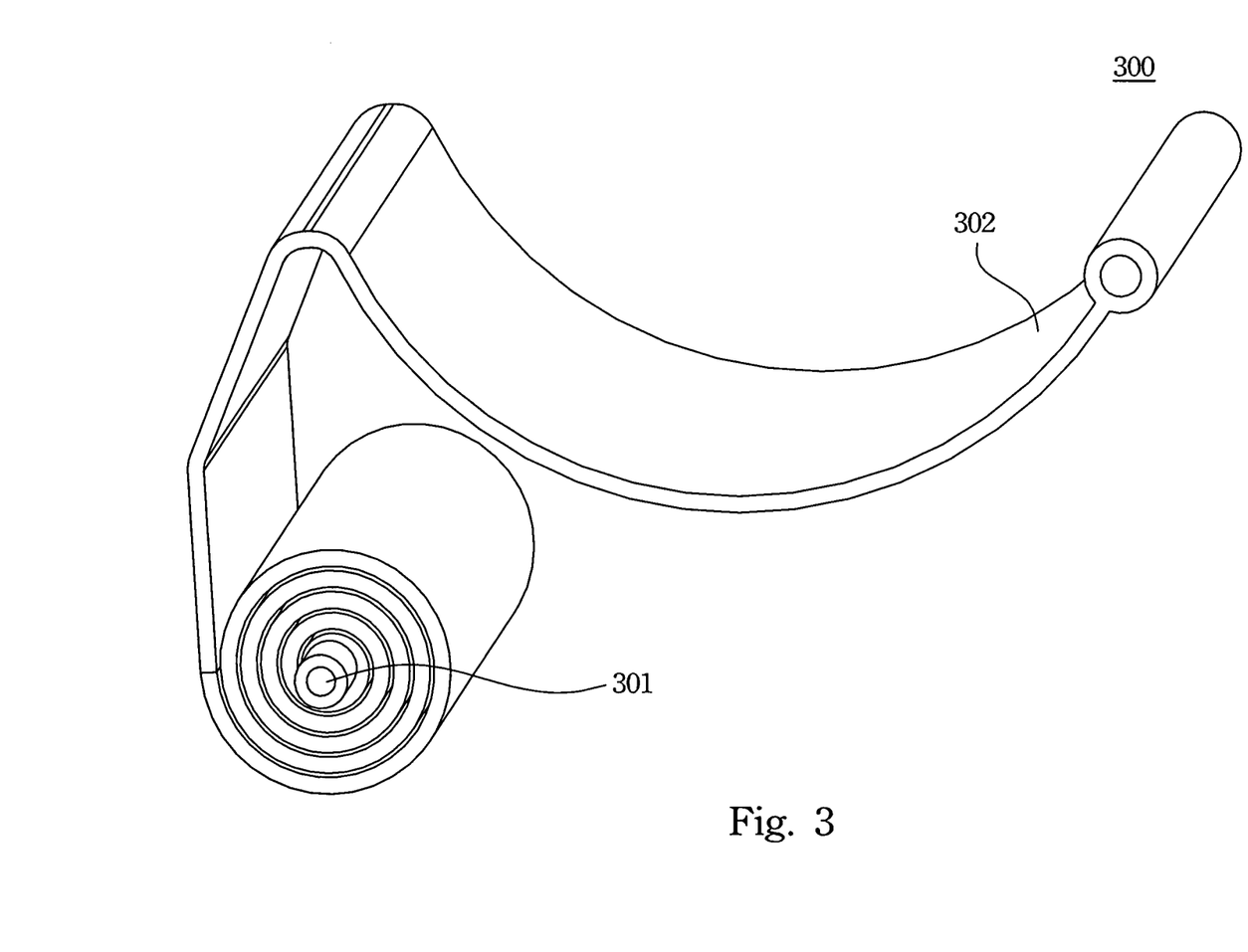
FIG. 3 is an appearance view of the reel-type cuff shown in FIG. 2.

Referring from FIG. 1 to FIG. 3, in which FIG. 1 is an appearance view of the blood pressure measuring device 100 of one embodiment of the present invention, when not being operated, FIG. 2 is a cross sectional view of FIG. 1 along a 2-2 section line, and FIG. 3 is an appearance view of the reel-type cuff 300 shown in FIG. 2.

The blood pressure measuring device 100 provided by the present invention comprises a base 200, a reel-type cuff 300 and plural stoppers 400a, 400b, 400c. In this embodiment, the base 200 is hollow and an accommodating space 210 is formed therein for storing most of the reel-type cuff 300. The outer surface of the base 200 at least includes a first fastening part 220. The first fastening part 220 is disposed at one lateral side of the base 200. The reel-type cuff 300 is elastically and recoverably reeled in the accommodating space 210, and is capable of freely extending out of the accommodating space 210 from the base 200, and the extending end of the reel-type cuff 300 has a second fastening part 310 thereon. The second fastening part 310 is corresponding to the first fastening part 220 for the purpose of fastening. The stoppers 400 are respectively moveably installed on the base 200 for respectively limiting various determined lengths that the reel-type cuff 300 is extending out of the accommodating space 210 of the base 200 through physically contact or interference with the reel-type cuff 300 in the accommodating space 210. As such, by utilizing the various limited lengths that the reel-type cuff 300 is extending out from the base 200 for fitting users who have different arm sizes, the time and operation for reeling the cuff 300 on an arm are reduced and simplified, and the arm can be efficiently placed at a proper location on the cuff 300 for increasing the precision of blood pressure measurement.

Substantially, the accommodating space 210 of the base 200 is further installed with two guiding posts 230a, 230b, abutted against the surface of the reel-type cuff 300. The exterior of the base 200 is further formed with an arc-shaped concave face 240, an opening 250 and a position limiting ring 260 thereon. The arc-shaped concave face 240 is disposed on a top of the base 200 so that a user can place a measured object thereon, e.g. an arm or of human being. The position limiting ring 260 is on a side, away from the first fastening part 220, of the arc-shaped concave face 240. The opening 250 is on another side, close to the first fastening part 220, of the arc-shaped concave face 240.

The function of the reel-type cuff 300 is the same as the mentioned artery pressing bag for reeling the measured object to measure the blood pressure. The reel-type cuff 300 has a first end 301 and a second end 302 opposite to the first end 301. The reel-type cuff 300 is able to be elastically and recoverably reeled with the first end 301 in the accommodating space 210, and the moving direction of the reel-type cuff 300 is altered through the guiding posts 230 and guided to move towards the opening 250. The second end 302 of the reel-type cuff 300 extends out from the opening 250 of the base 200 and passes through the arc-shaped concave face 240 to the position limiting ring 260 where the second end 302 is kept out of the opening 250 and temporarily fastened by the position limiting ring 260.

Figure 4:
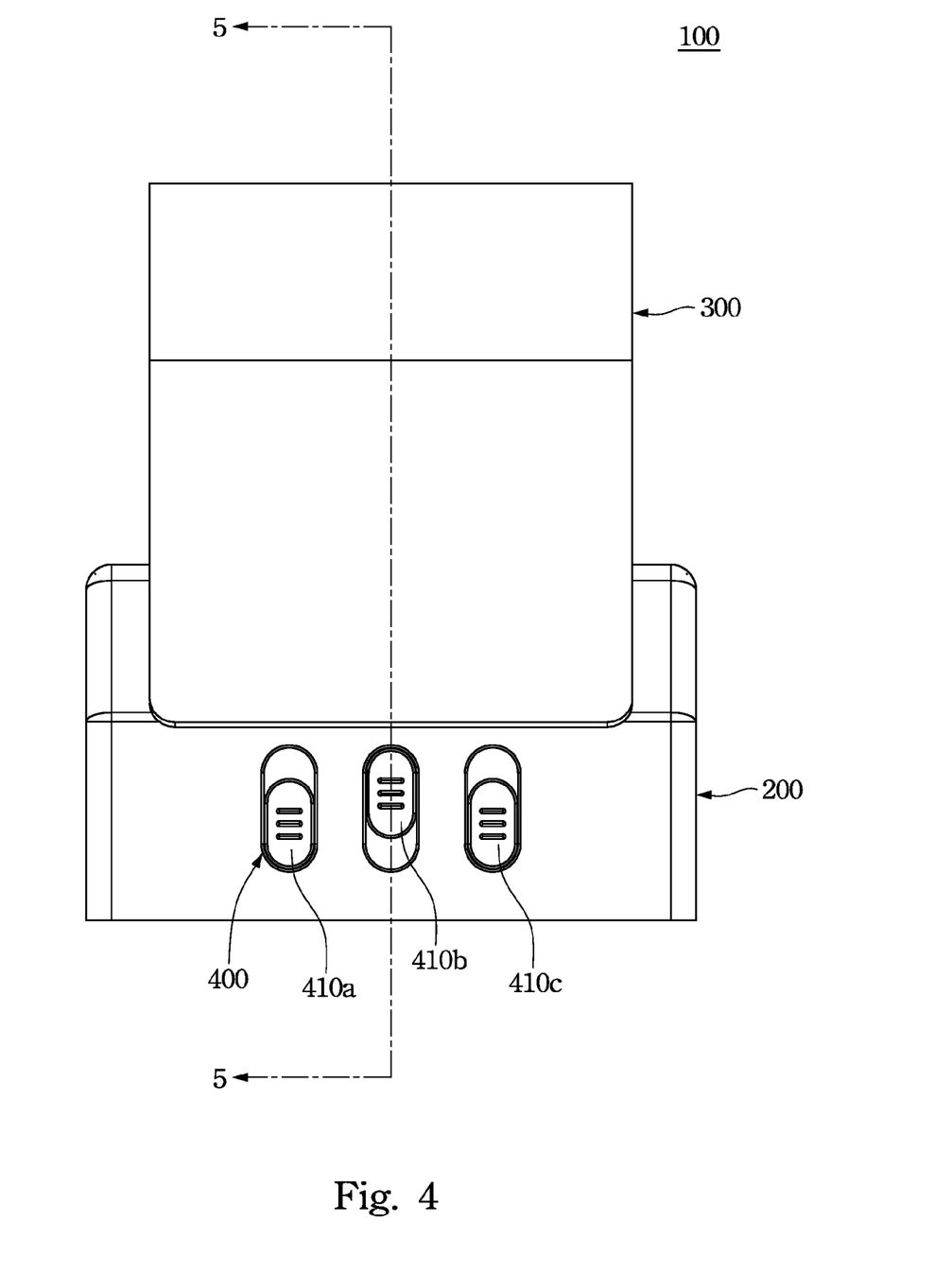
FIG. 4 is a side view illustrating the blood pressure measuring device of this embodiment while being operated.
Figure 5:
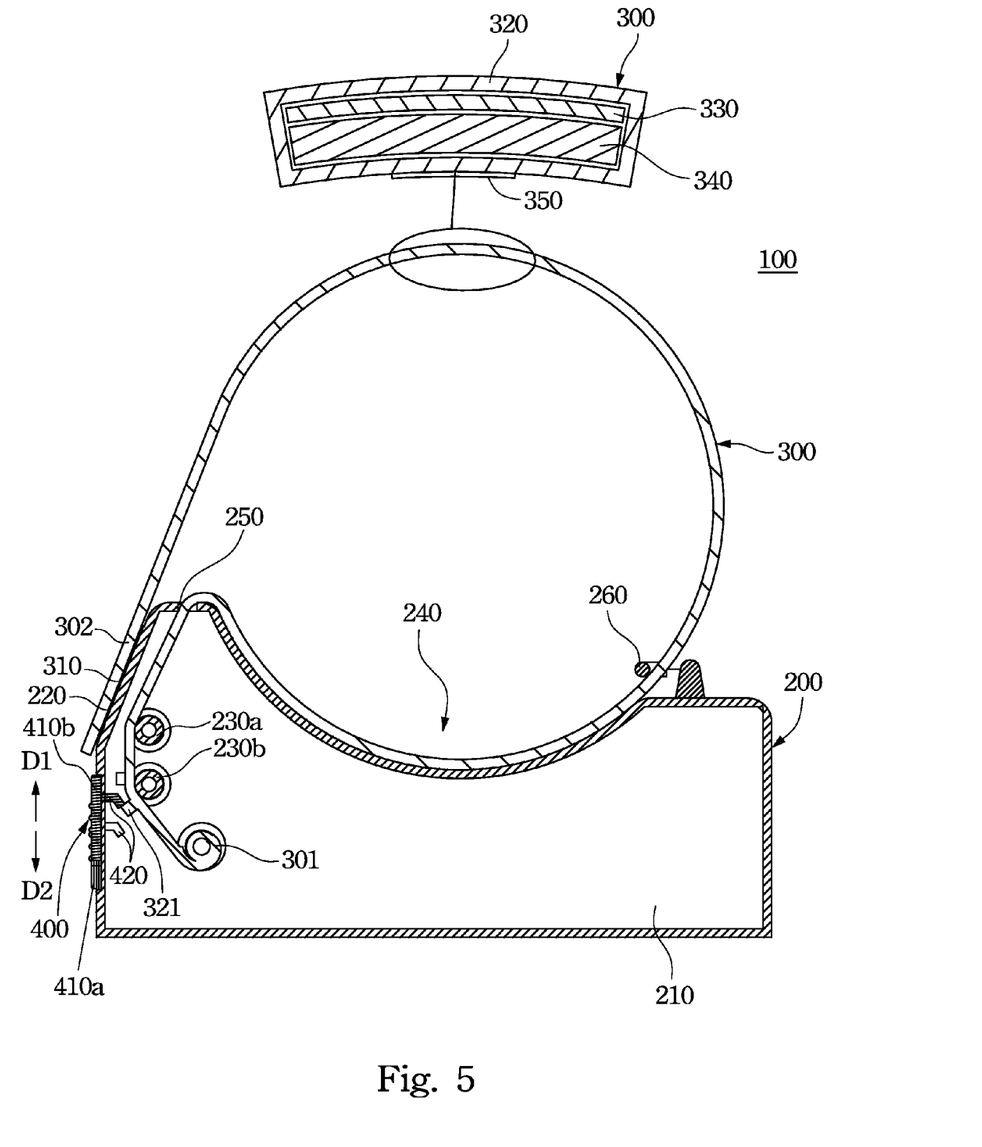
FIG. 5 is a cross sectional view of FIG. 4 along a 5-5 section line.
Figure 6:
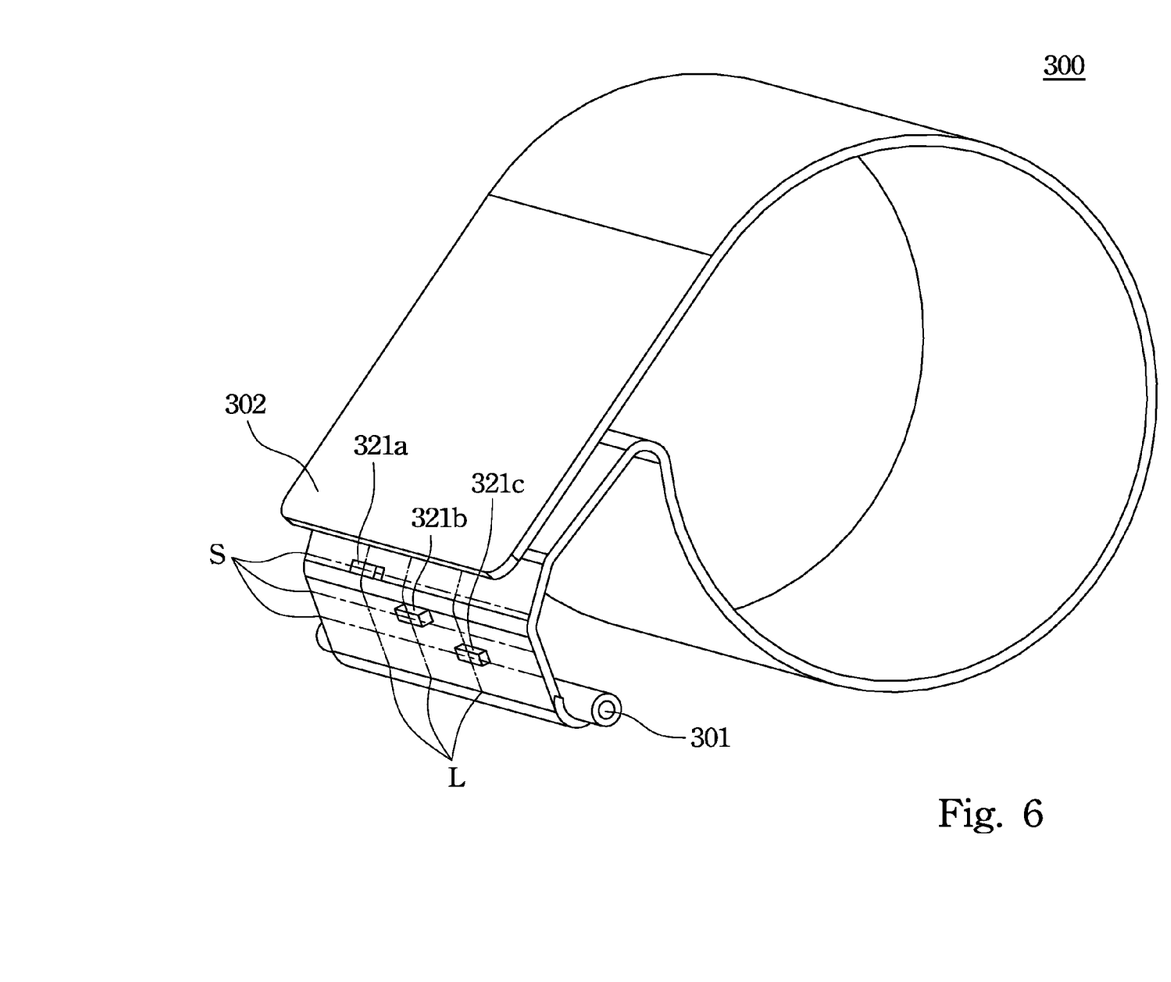
FIG. 6 is an appearance view of the reel-type cuff shown in FIG. 5.

Referring from FIG. 4 to FIG. 6, wherein FIG. 4 is a side view illustrating the blood pressure measuring device of this embodiment while being operated; FIG. 5 is a cross sectional view of FIG. 4 along a 5-5 section line; FIG. 6 is an appearance view of the reel-type cuff 300 shown in FIG. 5.

The reel-type cuff 300 includes a strip-shaped band 320, a strip-shaped resilient sheet 330 and an inflation bag 340. The second fastening part 310 is installed on the second end 302 of the reel-type cuff 300, and is disposed on a surface of the strip-shaped band 320 outside the base 200.

The strip-shaped resilient sheet 330 is longitudinally installed (embedded) in the strip-shaped band 320 along the direction from the first end 301 to the second end 302. The inflation bag 340 is also longitudinally installed (embedded) in the strip-shaped band 320 along the direction from the first end 301 to the second end 302. Besides, the inflation bag 340 is stacked on the strip-shaped resilient sheet 330 and is disposed on the side of the strip-shaped band 320 which is neighbored to the measured object. Moreover, the length of the inflation bag 340 is less than that of the strip-shaped resilient sheet 330. The strip-shaped band 320 is printed with an artery marker 350, which is substantially corresponding to the central location of the inflation bag 340.

When the second end 302 of the reel-type cuff 300 starts to be continuously reeled out for being spaced away from the position limiting ring 260, more of the reel-type cuff 300 is continuously extended from the opening 250, the strip-shaped resilient sheet 330 in the first end 301 of the reel-type cuff 300 is forced to gradually stretch (as shown in FIG. 6) from a reeled status (as shown in FIG. 3), meanwhile a recovery elastic force is generated for recovering to the reeled status. When the second end 302 of the reel-type cuff 300 reels the measured object from one side of the arc-shaped concave face 240 to the first fastening part 220 located at the other side of the arc-shaped concave face 240, the second end 302 can be fastened on the first fastening part 220 through the second fastening part 310 (as shown in FIG. 5).

At this time, the reel-type cuff 300 is able to firmly reel the measured object via the recover elastic force generated at the first end 301 of the reel-type cuff 300, and then the inflation bag 340 starts to be inflated. When the second fastening part 310 is released from the first fastening part 220, the reel-type cuff 300 starts to retract in the accommodating space 210 via the recover elastic force, till the second end 302 is stopped by the position limiting ring 260 (as shown in FIG. 2).

Accordingly, the reel-type cuff 300 can be rapidly installed on the arm, and after the measurement is finished, the reel-type cuff 300 can be rapidly stored, thus reducing the whole processing time of blood pressure measurement.

Moreover, the length that the reel-type cuff 300 extended out is sufficient enough to reel the user's arm (as shown in FIG. 5), thus no excess length thereof is left like the conventional arts which may obstruct the process of blood pressure measurement. With the feature that the reel-type cuff 300 capable of being recovered and reeled that after the reel-type cuff 300 is released from the arm, most of the reel-type cuff 300 is able to be rapidly stored in the base 200 (as shown in FIG. 2), a better appearance and easier storage are therefore provided, and a space that contains the device can be smaller and the time for managing the cuff can be also saved.

Referring to FIG. 5 and FIG. 6, the reel-type cuff 300 is further provided with a plurality of limiting blocks 321 arranged on a surface of the strip-shaped band 320 in the accommodating space 210 and respectively corresponding to one of the stoppers 400. Anyone of the stoppers 400 can be operated to contact or interfere against the corresponding limiting block 321 for limiting the motion of the reel-type cuff 300, which in turns limiting the certain length that the reel-type cuff 300 extended out from the base 200.

Substantially, the surface of the reel-type cuff 300 installed with the limiting blocks 321 can be defined with a plurality of long axles L thereon and a plurality of short axles S thereon. The long axles L thereon are parallel to each other, and the short axles S are perpendicular to the long axles L. The long axles L are defined as the length direction of the reel-type cuff 300 while the short axles S are defined as the width direction of the reel-type cuff 300. The limiting blocks 321 are respectively arranged to align with different long axles L, and any two of the limiting blocks 321 are not arranged to align with the same short axle S. In other words, only one of the mentioned stoppers 400 would be in contact (i.e. abutted against) with its own corresponding limiting block 321 at a certain time, even there are two or more stoppers are operated.

Referring to FIG. 4 and FIG. 5, in this embodiment, the stopper 400 can alternatively be practiced as a slide button 410a, 410b, 410c. The slide button 410 is installed on the surface of the base 200 for moving repeatably along a direction parallel to the surface of the base, and one side of the slide button 410 is exposed outside the surface of the base 200, the other side of the slide button 410 is connected with a first tenon 420. The first tenon 420 passes through a slit of the base 200 into the accommodating space 210 for moving together with the slide button 410 onto a traveling path of the corresponding limiting block 321 that moves with the reel-type cuff 300.

In operation, when one of the slide buttons 410 moves towards a first direction D1, the first tenon 420 thereof is driven to a pre-position that is on a traveling path of a corresponding limiting block 321a, 321b, 321c when moves with the reel-type cuff 300. As such, when the reel-type cuff 300 is pulled out from the accommodating space 210 of the base 200, the corresponding limiting block 321 is moved along the mentioned traveling path to a certain distance, the mentioned limiting block 321 is blocked by the first tenon 420, so the reel-type cuff 300 is no longer able to be pulled out from the base 200, thus achieving the purpose of substantially limiting the length that the reel-type cuff 300 extended out from the accommodating space 210 of the base 200. When the slide button 410 moves towards a second direction D2, the first tenon 420 thereof is drived to move away from the traveling path, such that the corresponding limiting block 321 is no longer blocked.

Figure 7:
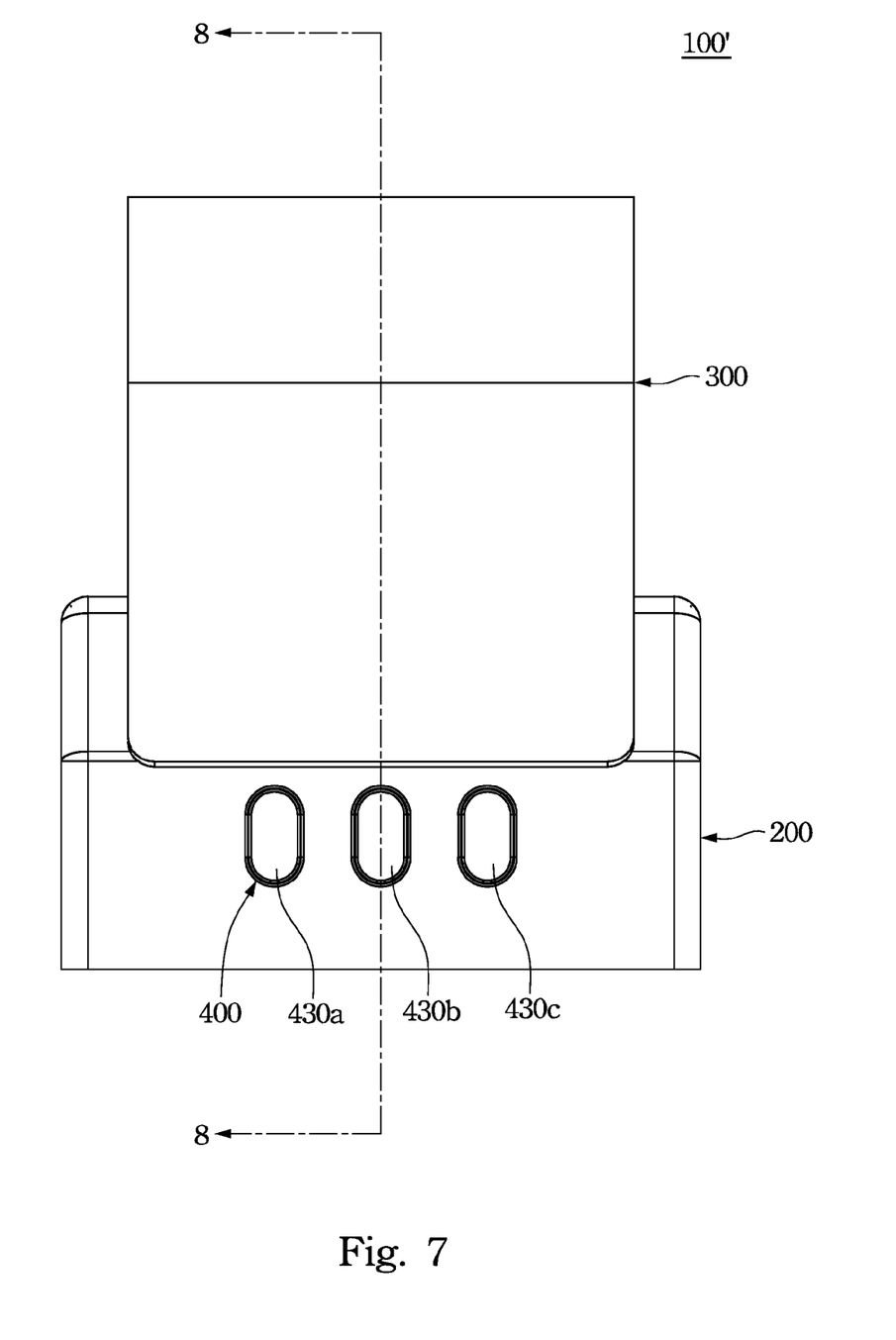
FIG. 7 is a schematic view illustrating an alternative according to this embodiment of the blood pressure measuring device of the present invention.
Figure 8:
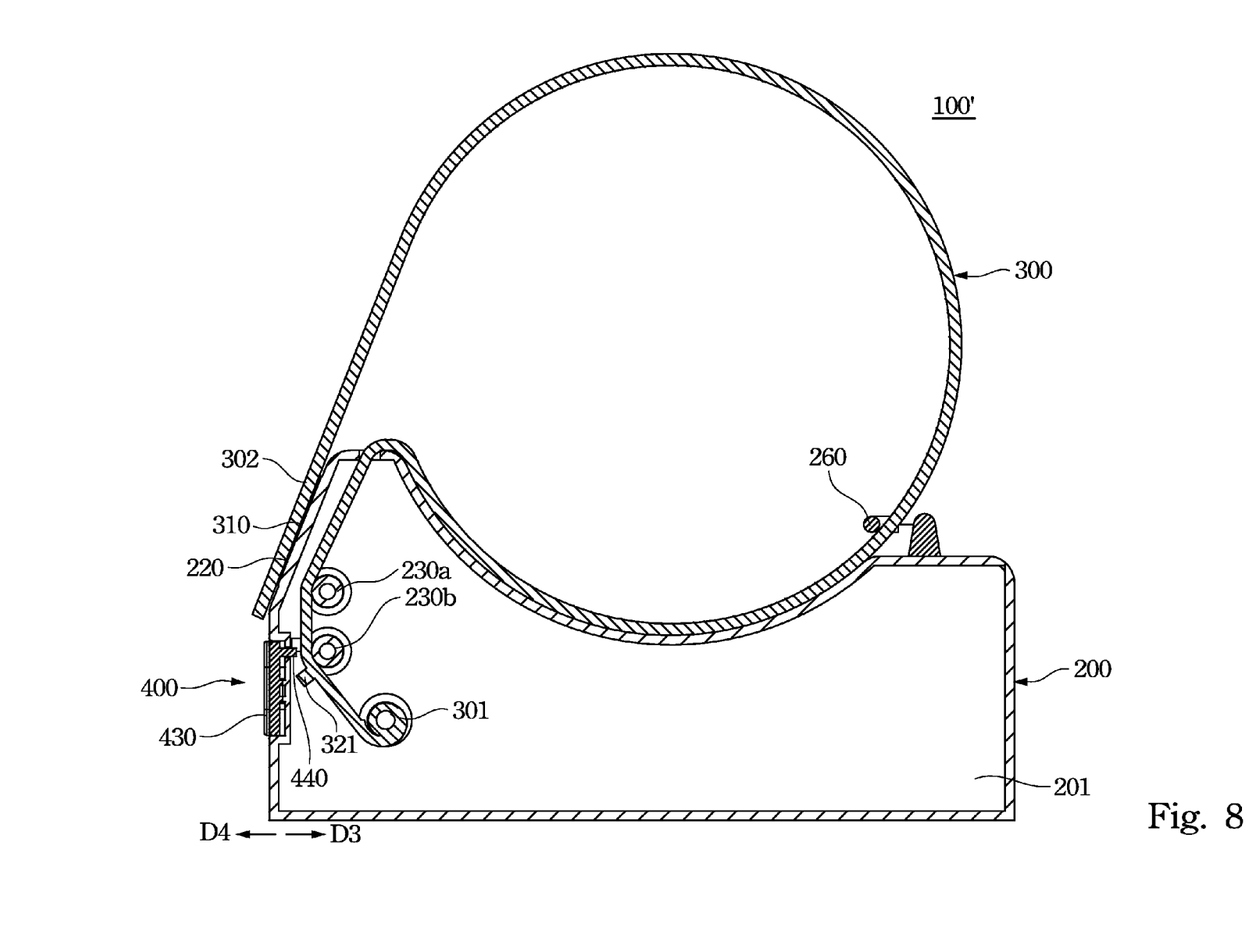
FIG. 8 is a cross sectional view of FIG. 7 along an 8-8 section line.

Referring to FIG. 7 and FIG. 8, wherein FIG. 7 is a schematic view illustrating an alternative according to this embodiment of the blood pressure measuring device 100' of the present invention; and FIG. 8 is a cross sectional view of FIG. 7 along an 8-8 section line.

In this embodiment, the stopper 400 alternatively can be practiced as a press button 430a, 430b, 430c. The press button 430 is installed on the base 200 for repeatably moving in/out the base 200 along a direction perpendicular to the surface of the base 200, and one side of the press button 430 is exposed outside the surface of the base 200, the other side of the press button 430 is connected with a second tenon 440. The second tenon 440 passes through an orifice of the base 200 into the accommodating space 210 for moving together with the press button 430 onto a traveling path of the corresponding limiting block 321 that moves with the reel-type cuff 300.

In operation, when one of the press buttons 430 moves towards a third direction D3, the second tenon 440 thereof is drived to a pre-position that is on the traveling path of a corresponding limiting block 321.

As such, when the reel-type cuff 300 is pulled out from the accommodating space 210 of the base 200, the corresponding limiting block 321 is moved along the mentioned traveling path to a certain distance, then the mentioned limiting block 321 is blocked by the second tenon 440, so the reel-type cuff 300 is no long able to be pulled out from the base 200, thus achieving the purpose of substantially limiting the length that the reel-type cuff 300 extended out from the base 200. When the press button 430 moves towards a fourth direction D4, the second tenon thereof 440 is drived to move away from the traveling path, so the corresponding limiting block 321 is no longer blocked. Moreover, a spring (not shown) is further provided between the press button 430 and the base 200 for assisting the press button 430 moving towards the fourth direction D4.

Because relative positions of the stoppers 400 and the limiting blocks 321 are well defined when being designed, different stoppers 400 are operated to be abutted against its corresponding limiting blocks 321 so as to provide different lengths that the reel-type cuff 300 extended out from the base 200 for fitting users having various arm sizes.

For example, referring to FIG. 4 and FIG. 6, when the blood pressure measuring device 100 is designed to be equipped with three different lengths that the reel-type cuff 300 can be extended out from the base 200, for respectively fitting users with large, medium or small arm sizes, the surface of the reel-type cuff 300 can be installed with three limiting blocks 321 arranged with the mentioned fashion and respectively defined as a first limiting block 321, a second limiting block 321 and a third limiting block 321 (as shown in figures being viewed from right to left), and the base 200 is installed with the stoppers 400, having the same amount as the limiting locks 321, and respectively defined as a first stopper 400, a second stopper 400 and a third stopper 400 (as shown in figures being viewed from right to left) and respectively corresponding to the first limiting block 321, the second limiting block 321 and the third limiting block 321.

Accordingly, when a user having a medium arm size is processed with the blood pressure measurement, the user only has to operate the second stopper 400 arranged in the middle, so that the second stopper 400 can be abutted against the second limiting block 321 after the reel-type cuff 300 is pulled from the base 200 to a certain length, and the certain length matches medium arm size; at this time, the second fastening part 310 processes a fastening action with respect to the first fastening part 220. Moreover, the length of medium arm size enables the artery marker 350 on the reel-type cuff 300 being substantially aimed at the arm artery, such that the inflation bag 340 can sufficiently press the arm artery, so as to increase the precision of blood pressure measurement.

Therefore, when a user uses the blood pressure measuring device to measure its blood pressure for the first time, the user just to select and move a suitable slide button 410 towards the first direction D1 and then fastens the slide button 410 through the first fastening part 220 together with the second fastening part 310 once contact or interfere occurs, the reel-type cuff 300 can provide a suitable length for the user. Moreover, as long as the slide button 410 is not moved back or the user remembers the one of the slide buttons 410 suitable to him/her, a function of memorizing the suitable length of the reel-type cuff 300 for the user is therefore provided whenever the reel-type cuff 300 of the blood pressure measuring device 100 is reeled out. So for a user, there is no need of adjusting the required length of the reel-type cuff 300 in every operation, so the precision of blood pressure measurement is ensured.

Referring to FIG. 2 and FIG. 5, in another embodiment of the present invention, the first fastening part 220 is a first hook-and-loop unit (e.g. Velcro unit with hooks or loops), the second fastening part 310 is a second hook-and-loop unit (e.g. Velcro unit with hooks or loops); the second hook-and-loop unit and the first hook-and-loop unit are matched so as to adhere to each other.

As mentioned above, the blood pressure measuring device provided by the present invention not only can rapidly assist the arm artery to be aimed at the proper position of the pressing bag for increasing the precision of blood pressure measurement, but also reducing the testing time for reeling the pressing bag on the arm of various users having different arm sizes so as to increase convenience of using the blood pressuring measuring device. Moreover, the blood pressure measuring device of the present invention has also improved the storage of the pressing bag for shortening the packing/storing time for the blood pressure measuring device.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. A blood pressure measuring device, comprising:
a base having an accommodating space therein and a first fastening part thereon;
a reel-type cuff having a first end and a second end opposite to the first end, the reel-type cuff elastically and recoverably reeled the accommodating space with the first end thereof, the second end being reeled out of the accommodating space, and having at least one limiting block arranged on a surface of the reel-type cuff in the accommodating space;

a second fastening part installed on the second end of the reel-type cuff for being fastened on the first fastening part; and at least one stopper, comprising:
  a slide button movably installed on a surface of the base for moving along a direction parallel to the surface of the base; and
  a tenon installed on one side of the slide button extending to the accommodating space and capable of moving together with the slide button onto a traveling path of the at least one limiting block that moves with the reel-type cuff,
wherein the stopper is capable of limiting at least one determined length that the reel-type cuff is extended out from the accommodating space when the stopper is physically contacted with the at least one limiting block of the reel-type cuff in the accommodating space.

2. The blood pressure measuring device as claimed in claim 1, wherein the at least one limiting block comprises a plurality of limiting blocks, wherein the plurality of the limiting blocks are respectively arranged to align with different long axles which are parallel with each other and defined on the surface of the reel-type cuff, and any two of the plurality of limiting blocks are not arranged to align with a same short axle which is perpendicular to the long axles and defined on the surface of the reel-type cuff.

3. The blood pressure measuring device as claimed in claim 1, wherein the reel-type cuff comprises:
  a strip-shaped band;
  a strip-shaped resilient sheet longitudinally installed in the strip-shaped band; and
  an inflation bag longitudinally installed in the strip-shaped band and stacked on the strip-shaped resilient sheet.

4. The blood pressure measuring device as claimed in claim 1, wherein at least one guiding post is formed in the accommodating space of the base for altering a moving direction of the reel-type cuff.

5. The blood pressure measuring device as claimed in claim 1, wherein the base is provided with an arc-shaped concave face for placing a measured object thereon.

6. The blood pressure measuring device as claimed in claim 1, wherein the first fastening part is a first hook-and-loop unit, the second fastening part is a second hook-and-loop unit mutually adhered with the first hook-and-loop unit.

7. The blood pressure measuring device as claimed in claim 1, wherein the base further comprises:
  a position limiting ring installed on a top of the base for limiting the reel-type cuff.

8. A blood pressure measuring device, comprising:
a base having an accommodating space therein and a first fastening part thereon;
a reel-type cuff having a first end and a second end opposite to the first end, the reel-type cuff elastically and recoverably reeled in the accommodating space with the first end thereof, the second end being reeled out of the accommodating space, and having at least one limiting block arranged on a surface of the reel-type cuff in the accommodating space;
a second fastening part installed on the second end of the reel-type cuff for being fastened on the first fastening part; and
at least one stopper, comprising:
  a press button movably installed on the base for moving along a direction perpendicular to the surface of the base; and
  a tenon installed on one side of the press button extending to the accommodating space and capable of moving together with the press button onto a traveling path of the at least one limiting block that moves with the reel-type cuff,
wherein the stopper is capable of limiting at least one determined length that the reel-type cuff is extended out from the accommodating space when the stopper is physically contacted with the at least one limiting block of the reel-type cuff in the accommodating space.

9. The blood pressure measuring device as claimed in claim 8, wherein the at least one limiting block comprises a plurality of limiting blocks, wherein the plurality of the limiting blocks are respectively arranged to align with different long axles which are parallel with each other and defined on the surface of the reel-type cuff, and any two of the plurality of limiting blocks are not arranged to align with a same short axle which is perpendicular to the long axles and defined on the surface of the reel-type cuff.

10. The blood pressure measuring device as claimed in claim 8, wherein the reel-type cuff comprises:
  a strip-shaped band;
  a strip-shaped resilient sheet longitudinally installed in the strip-shaped band; and
  an inflation bag longitudinally installed in the strip-shaped band and stacked on the strip-shaped resilient sheet.

11. The blood pressure measuring device as claimed in claim 8, wherein at least one guiding post is formed in the accommodating space of the base for altering a moving direction of the reel-type cuff.

12. The blood pressure measuring device as claimed in claim 8, wherein the base is provided with an arc-shaped concave face for placing a measured object thereon.

13. The blood pressure measuring device as claimed in claim 8, wherein the first fastening part is a first hook-and-loop unit, the second fastening part is a second hook-and-loop unit mutually adhered with the first hook-and-loop unit.

14. The blood pressure measuring device as claimed in claim 8, wherein the base further comprises:
  a position limiting ring installed on a top of the base for limiting the reel-type cuff.

\* \* \* \* \*